United States Patent [19]

Schnur

[11] 4,226,875

[45] Oct. 7, 1980

[54] NOVEL SPIRO-OXAZOLIDINEDIONES

[75] Inventor: Rodney C. Schnur, Noank, Conn.

[73] Assignee: Pfizer Inc., New York, N.Y.

[21] Appl. No.: 26,615

[22] Filed: Apr. 2, 1979

[51] Int. Cl.$^2$ .................... C07D 263/44; A61K 31/42
[52] U.S. Cl. ..................................... 424/272; 548/216
[58] Field of Search ................... 260/307 B; 548/108, 548/216; 424/272

[56] References Cited

PUBLICATIONS

R. W. Stoughton, J.A.C.S. 63, 2376, (1941).
J. W. Clark-Lewis, Chemical Reviews 58, 63, (1958).
M. A. Spielman, J.A.C.S. 66, 1244, (1944).
H. Najer et al., Bull. Soc. Chim., Fr. 1961, 1226, (1961).

*Primary Examiner*—Jose Tovar
*Attorney, Agent, or Firm*—Francis X. Murphy; Charles J. Knuth; Peter C. Richardson

[57] ABSTRACT

Novel spiro-oxazolidinediones useful as aldose reductase inhibitors and as therapeutic agents for the treatment of chronic diabetic complications are disclosed. Pharmaceutical compositions containing the novel compounds and a method of treating chronic diabetic complications are also disclosed.

9 Claims, No Drawings

NOVEL SPIRO-OXAZOLIDINEDIONES

BACKGROUND OF THE INVENTION

This invention relates to novel spiro-oxazolidindiones useful in the treatment of certain chronic complications arising from diabetes mellitus, such as diabetic cataracts retinopathy and neuropathy, to intermediates for the preparation thereof, to pharmaceutical compositions containing such compounds and to a method of using these compounds.

In the past various attempts have been made to obtain more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, of peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel spiro-oxazolidinediones of the formula

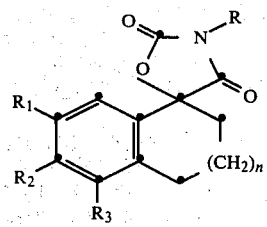

and the pharmaceutically acceptable salts thereof, wherein n is zero or one; R and $R_2$ are each hydrogen; and $R_1$ and $R_3$ are each selected from the group consisting of hydrogen, chloro, bromo, fluoro and alkyl of 1 to 3 carbon atoms. Additionally, for the purposes of this invention, compounds wherein R is alkyl of 1 to 4 carbon atoms, benzyl or substituted benzyl, wherein $R_2$ is chloro, bromo, fluoro or alkyl of 1 to 3 carbon atoms, and wherein $R_1$, $R_2$ or $R_3$ are phenyl or substituted phenyl are regarded as equivalent to the compounds having R, $R_1$, $R_2$ and $R_3$ groups as previously defined and are within the scope of this invention.

A preferred group of compounds is that wherein n is one. Preferably, $R_1$ and $R_3$ are each selected from the group consisting of hydrogen, chloro, bromo, fluoro and methyl, most preferably hydrogen.

A further group of compounds of interest are those wherein n is zero. Preferably $R_1$ and $R_3$ are each selected from the group consisting of hydrogen, chloro, bromo, fluoro and methyl, most preferably hydrogen.

Also within the scope of the present invention are intermediates useful for the preparation of the spirooxazolidinediones of formula I. Thus, the present invention includes compounds of the formula

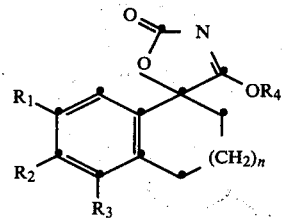

wherein $R_1$, $R_2$, $R_3$, and n are as previously defined, and $R_4$ is selected from alkyl of 1 to 4 carbon atoms and benzyl.

Further intermediates of the present invention are those compounds of the formula

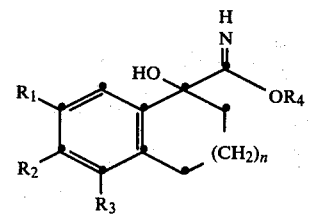

wherein $R_1$, $R_2$, $R_3$, $R_4$, and n are as previously defined.

Preferred compounds of formulae II and III are those useful for the preparation of the preferred spirooxazolidinediones of this invention, as previously described herein i.e. those having the corresponding preferred values for $R_1$, $R_2$, $R_3$, and n. Preferably, $R_4$ is alkyl of 1 to 3 carbon atoms, most preferably ethyl.

Further intermediates of the present invention are those of the formula

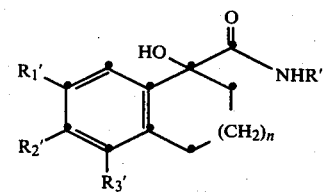

wherein n is as previously defined and $R_1'$ and $R_3'$ are each selected from hydrogen, chloro and alkyl of 1 to 3 carbon atoms; $R'$ and $R_2'$ are each hydrogen. Additionally, compounds wherein $R'$ is alkyl of 1 to 4 carbon atoms or benzyl and wherein $R_2'$ is chloro or alkyl of 1 to 3 carbon atoms are regarded for the purposes of the present invention as equivalent to the compounds of formula IV previously defined and are within the scope of this invention.

The present invention further comprises a novel method for the treatment of a diabetic host to prevent or alleviate diabetes-associated complications, such as cataracts, neuropathy or retinopathy, which method comprises administering to the host an effective amount of a compound of formula I.

Also embraced by the present invention are pharmaceutical compositions comprising a pharmaceutically acceptable carrier and a compound of formula I in an amount effective to prevent or alleviate diabetes-associated complications, such as cataracts, neuropathy or retinopathy, including compositions for oral, parenteral or topical administration.

DETAILED DESCRIPTION OF THE INVENTION

The novel spiro-oxazolidinediones of formula I are prepared from appropriately substituted ketones of the formula

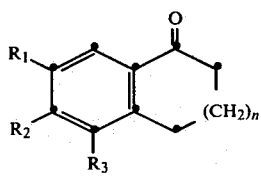

V where $R_1$, $R_2$, $R_3$, and n are as previously defined. Such compounds are readily available or may be synthesized by conventional routes.

The reaction sequence for formation of compounds of formula I is shown in reaction scheme A, to which reference is made for the following discussion. By way of exemplification, the nomenclature used in the following discussion refers to compounds wherein n is 1. However, it will be understood that the analogous compounds wherein n is zero will also be formed by the reactions described hereinafter from the appropriate ketone starting material. The ketone 1a is first reacted with a trialkylsilyl cyanide, $(R')_3SiCN$, to form the 1-cyano-1-trialkylsilyloxy derivative 2a. A preferred trialkylsilyl cyanide for use in this reaction is trimethylsilyl cyanide, although other lower trialkylsilyl cyanides having from 1 to 4 carbon atoms in each alkyl group may be employed. The reaction is conducted in the presence of a Lewis acid catalyst, such as a zinc halide, aluminum halide or boron trifluoride, with zinc iodide being a preferred catalyst. Temperatures in the range of about 0° C. to about 50° C. are generally employed, preferably about 0° C. to 20° C., in an inert organic solvent, typically an ether such as diethyl ether, dimethoxyethane, tetrahydrofuran, dioxane and the like, or a halocarbon such as methylene chloride, chloroform Scheme A

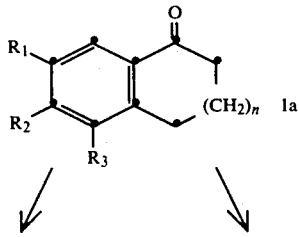

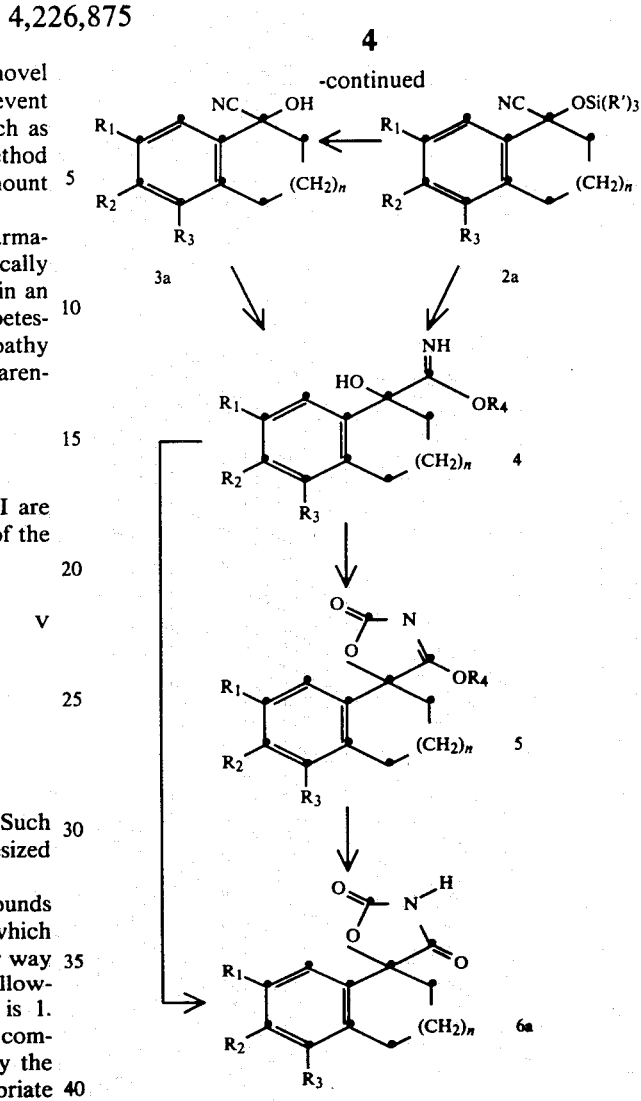

and similar solvents. Compound 2a is then converted to an alkyl 1-hydroxy-1-carboximidate derivative 4 by reaction with an acid in an alcohol solvent $R_4OH$. Suitable acids include hydrogen halides, especially hydrogen chloride. The alcohol $R_4OH$ may be either a lower alkanol of 1 to 4 carbon atoms, benzyl alcohol or a substituted benzyl alcohol, the substituent including chloro, bromo, fluoro, hydroxy, alkyl of 1 to 3 carbon atoms and alkoxy of 1 to 3 carbon atoms. The reaction is generally conducted at temperatures in the range of about −10° C. to about 25° C., preferably at about 0° C. to 10° C.

The 1-hydroxy-4-carboximidate derivative 4 may also be prepared from the ketone starting material 1a via the cyanohydrin derivative 3a. The latter is formed by reaction of the ketone with liquid hydrogen cyanide, in the presence of a base such as piperidine, pyridine and the like, at a temperature of about 0° C. to 50° C., preferably at about 0° C. to 10° C. following the procedure described by Stoughton, J.A.C.S. 63, 2376 (1941). The cyanohydrin is then converted to the 1-hydroxy-1-carboximidate derivative 4 using a hydrogen halide in alcohol solvent, as previously described for the conversion of 2a to 4.

The cyanohydrin 3a may also be formed from the 1-cyano-1-trialkylsilyloxy derivative 2a and may be isolated as an intermediate during the initial stages of the conversion of 2a to 4 by reaction with a hydrogen halide and an appropriate alcohol, as previously described.

The 1-hydroxy-4-carboximidate derivative 4 may be converted directly to the spiro-oxazolidin-2,4-dione 6a by a number of methods. In all cases, the spirooxazolin-2-one 5 is an intermediate and can, if desired, be isolated from the reaction mixture. However, it is generally preferred to convert 4 to 6a directly without such isolation of the intermediate 5. The 1-hydroxy-1-carboximidate may be reacted with phosgene in the presence of a base such as triethylamine, or other trialkylamines having from 1 to 4 carbon atoms in each alkyl group, in an inert organic solvent such as an ether, for example diethyl ether, tetrahydrofuran, dimethoxyethane, dioxane and the like. The phosgene is generally bubbled through the reaction solution at a temperature of about $-10°$ C. to about $10°$ C., for about 5 to 15 minutes and the solution is subsequently stirred at about $20°$ C. to $50°$ C., preferably at room temperature for about 12 to 48 hours, when the spiro-oxazolin-2-one 5 is predominantly formed. This intermediate may then be converted to the desired spiro-oxazolidin-2,4-dione 6a either by a further perfusion of phosgene at about $-10°$ C. to about $10°$ C. for about 15 to 75 minutes, followed by stirriang at room temperature for a further period of about 12 to 48 hours. Alternatively, an alkali metal carbonate, such as potassium or sodium carbonate, or ammonium carbonate can be added to a solution of the intermediate 5 in, for example, aqueous tetrahydrofuran, and stirred at a temperature of about $15°$ C. to about $50°$ C., preferably at about room temperature, for a period of about 6 to 24 hours to form the desired spiro-oxazolidin-2,4-dione.

The desired spiro-oxazolidin-2,4-dione can also be prepared from the 1-hydroxy-4-carboximidate derivative 4 by reaction with an alkyl haloformate, where the alkyl group is of 1 to 4 carbon atoms, a preferred reagent being ethyl chloroformate. The reaction is generally conducted by stirriang the intermediate 4, together with the alkyl haloformate in an inert solvent, such as pyridine, at a temperature of about $-10°$ C. to about $15°$ C., preferably at about $0°$ C. for a period of about 30 minutes to about 2 hours, followed by heating the solution to a higher temperature, about $50°$ C. to about $150°$ C., preferably about $90°$ C. to $120°$ C., for example to reflux temperature in pyridine, for about 2 to about 6 hours. If desired the spiro-oxazolidin-2-one intermediate 5 can be isolated from the initial reaction mixture after heating the solution for relatively shorter periods, for example about 1 hour.

The spirio-oxazolidin-2,4-diones can also be prepared from the intermediate 4 by reaction with 1,1'-carbonyldiimidazole, the reaction being generally conducted at a temperature of about $50°$ C. to $150°$ C., preferably about $80°$ C. to $110°$ C., neat or in an inert organic solvent such as dioxane, tetrahydrofuran, dimethoxyethane, dimethyl ether and the like, for a period of about 12 to 36 hours. If desired, the intermediate spiro-oxazolin-2-one 5 can be obtained by heating for only a relatively short period of time, for example about 30 minutes to about 90 minutes.

An alternative method of preparation available for certain of the substituted spiro-oxazolidin-2,4-diones of this invention is illustrated in reaction scheme B, to which reference is made for the following discussion. By way of exemplification, the nomenclature used in the following discussion refers to compounds wherein n is 1. However, it will be understood that the analogous compounds wherein n is zero will also be formed by the reactions described hereinafter from the appropriate ketone starting material. Starting materials are ketones of the formula 1b, wherein $R_1'$, $R_2'$ and $R_3'$ are selected from hydrogen, chloro and alkyl of 1 to 3 carbon atoms and n is as previously defined. The first step is the formation of either the 1-cyano-1-trimethylsilyloxy derivative 2b or the cyanohydrin 3b using the reaction conditions and reagents previously described for the conversion of 1a to 2a and 3a, respectively.

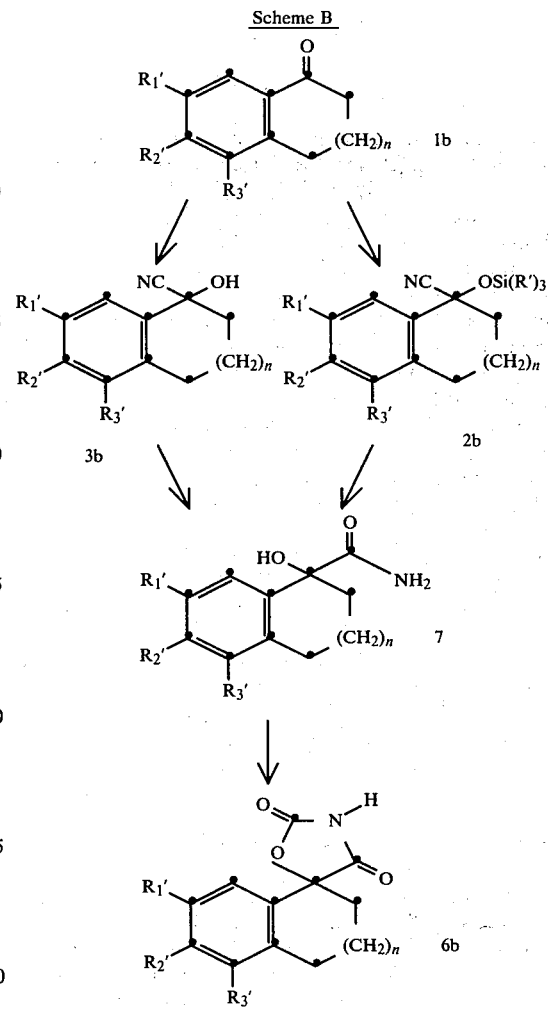

Scheme B

The intermediates 2b and 3b are converted to the amide 7 by treatment with acid such as concentrated hydrochloric or sulfuric acid in aqueous solution at a temperature between about $0°$ C. to about $30°$ C. For example, the reaction may be conducted by bubbling dry hydrogen chloride through a solution of either 2b or 3b in concentrated hydrochloric acid at about $0°$ C. to $5°$ C. for about 5 to 30 minutes, followed by stirring at about $15°$ C. to $30°$ C. for a period of about 6 to 24 hours.

The amide 7 may be converted to the desired spiro-oxazolidin-2,4-dione 6b by reaction with a dialkyl carbonate, such as diethyl carbonate, in the presence of an alkali metal alkoxide, for example sodium t-butoxide or potassium t-butoxide in a normal alkanol solvent having from 1 to 6 carbon atoms, for example n-butanol. The reaction is generally conducted by heating the mixture at about 70° C. to 150° C., preferably at about 100° C. to 125° C. for about 12 to 72 hours.

The amide 7 may also be converted to the desired spiro-oxazolidin-2,4-dione by reaction with ethyl chloroformate by procedures analogous to those described in Stoughton, J.A.C.S. 63, 2376 (1941).

Production of compounds of formula I wherein R is alkyl, or benzyl is effected by further reacting those compounds where R is hydrogen to introduce the desired substituent, using alkylation reactions well known in the art. For example, the compounds of formulae I wherein R is hydrogen may be reacted with an appropriate alkyl halide or benzyl halide in the presence of a base such as an alkali metal hydroxide, alkoxide or carbonate or a trialkylamine, such as triethylamine. The reaction is generally conducted at a temperature between about 0° C. and 140° C. in an inert solvent such as acetone, a lower alkyl alcohol, dimethyl formamide, an ether such as diethyl ether, tetrahydrofuran, dioxane, a halocarbon such as methylene chloride or chloroform and the like. Such compounds may also be prepared by similar reaction of the 1-hydroxy-1-carboximidate 4 of reaction scheme A to form a corresponding N-alkyl or N-benzyl substituted compound, followed by conversion to the N-substituted spiro-oxazolidin-2,4-dione, as described for the conversion of 4 to 6a.

Spiro-oxazolidin-2,4-diones of this invention formed as described above can be readily isolated from the reaction medium by conventional means, for example by evaporation of the solvent followed by extraction with ether and chloroform and recrystallization from toluene or a similar aromatic solvent.

Pharmaceutically acceptable salts can be readily prepared from compounds of formula I wherein R is hydrogen by conventional methods. Thus, these salts may be readily prepared by treating such spiro-oxazolidin-2,4-diones with an aqueous solution of the desired pharmaceutically acceptable cation and evaporating the resulting solution to dryness, preferably under reduced pressure. Alternatively, a lower alkanoic solution of the spiro-oxazolidin-2,4-dione may be mixed with an alkoxide of the desired metal and subsequently evaporating the solution to dryness. Suitable pharmaceutically acceptable cations for this purpose include, but are not limited to potassium, sodium, ammonium, calcium and magnesium.

It will be understood that the novel spiro-oxazolidin-2,4-diones of this invention contain an asymmetric center and thus will exhibit optical isomerism. If desired, the racemic spiro-oxazolidin-2,4-dione formed by the methods previously described can be resolved into the d- and l-isomeric forms by the application of conventional resolution methods. For example, adducts of one isomer with, for example cinchonidine, brucine, or l-amphetamine, may be formed and the free isomer obtained from such adducts by hydrolysis with aqueous acid. The other isomer can be recovered from the mother liquor after removal of the adduct described above.

If desired an optical isomer of either the d- or l- configuration may be converted to its corresponding epimer by methods analogous to those described by A. K. Bose, Tetrahedron Letters, 1973, 1619. Thus, the optical isomer obtained by the resolution methods described above is first treated with a base, such as an alkali metal hydroxide, such as sodium or potassium hydroxide, at about 0° to 100° C. in a solvent such as water, an alcohol, an ether, for example dioxane, or mixtures thereof. The spiro-oxazolidindione is thereby converted to the precursor 1-hydroxy-carboxamide (formula 7 shown in reaction Scheme B) of the same configuration as the initial spiro-oxazolidindione. This carboxamide 7 is then reacted with a dialkylazodicarboxylate, such as diethylazodicarboxylate or other lower alkyl analogues thereof in the presence of a trivalent phosphorous compound such as a triaryl phosphine, for example triphenyl phosphine, and a carboxylic acid such as formic acid or benzoic acid. The reaction is generally conducted at about 0° to 150° C. in an inert organic solvent such as tetrahydrofuran. The product from this reaction is the ester of the corresponding epimeric 1-hydroxyl-carboxamide i.e. the formate or benzoate esters of the carboxamide of formula 7 epimerized at the 1-position. The ester group is then hydrolyzed by treatment with a base such as an alkali metal hydroxide to form the 1-hydroxy-carboxamide of formula 7 epimerized at the 1-position i.e. of opposite configuration to the initial resolved spiro-oxazolidindiones. The epimerized 1-hydroxy-carboxamide is then converted to the epimer of the initial spiro-oxazolidindiones by the methods described previously for the conversion of 7 to 6b. Racemization may occur to some extent during the above sequence of reactions. The desired optical isomer may then be obtained by employing conventional resolution methods.

The novel spiro-oxazolidin-2,4-diones of this invention are useful as aldose reductase inhibitors, and as such are of therapeutic value in the treatment of chronic complications of diabetes, such as cataracts, retinopathy and neuropathy. As used in the claims and specification hereof, treatment is meant to include the prevention or alleviation of such conditions. The compounds may be administered to a subject in need of treatment by a variety of conventional routes of administration, including orally, parenterally and topically. In general these compounds will be administered at doses between about 1 and 250 mg per kg. body weight of the subject to be treated per day, preferably at about 1 to 100 mg/kg per day. However, some variation in dosage will necessarily occur depending on the condition of the subject being treated and the particular compound employed and the physician will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various non-toxic organic solvents. The pharmaceutical compositions formed by combining a spiro-oxazolidin-2,4-dione and the pharmaceutically acceptable carrier are then readily administered in a variety of dosage forms such as tablets, powders, lozenges, syrups, injectable solutions and the like. These pharmaceutical compositions can, if desired, contain additional ingredients such as flavorings, binders, excipients and the like. Thus for oral administration, tablets containing various excipients such as sodium citrate, calcium carbonate and calcium phosphate may be employed along with various disintegrants such as starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules; preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and if desired, emulsifying or suspending agents, together with diluents such as water, ethanol, propylene glycol, glycerin and combinations thereof.

For parenteral administration, solutions of the spiro-oxazolidin-2,4-diones in sesame or peanut oil or in aqueous propylene glycol may be employed, as well as sterile aqueous solutions of the corresponding water-soluble alkali metal or alkaline earth metal salts previously described. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily obtainable by standard techniques well known to those skilled in the art. It is also possible to administer a spiro-oxazolidin-2,4-diones topically, by use of an appropriate ophthalmic solution, which may then be administered dropwise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats. Suitable experimental procedures are described in U.S. Pat. No. 3,821,383 and the references cited therein.

In accord with the foregoing pharmacological tests, the activity of certain compounds of this invention has been tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-4}$ M are expressed as percent inhibition of enzyme activity. In this test spiro-[indane(1,5')oxazolidine]-2',4'-dione and 1',2',3',4'-tetrahydro-spiro-[oxazolidine(5,1')naphthalene]-2,4-dione gave 81% and 75% inhibition of the enzyme activity, respectively. From the results of this test it is to be expected that these compounds will exhibit activity in the other tests described above when administered in appropriate dosage amounts. Thus, for example, the compounds may be tested for their ability to reduce or inhibit sorbitol accumulation in the sciatic nerve of streptozotocinized (i.e., diabetic) rats by the procedure essentially described in U.S. Pat. No. 3,821,383. The amount of sorbitol accumulation in the sciatic nerves is measured 27 hours after induction of diabetes. The compounds are administered orally at appropriate dose levels at 4, 8 and 24 hours following the administration of streptozocin. The results obtained in this manner are expressed in terms of percent inhibition afforded by the test compound as compared to the case where no compound was administered (i.e., the untreated animal, where sorbitol levels normally rise from approximately 50–100 mM/g. tissue to as high as 400 mM/g. tissue in the 27-hour test period). In this test it is to be expected that spiro-[indane(1,5') oxazolidine]-2',4'-dione will exhibit activity when administered in doses of about 25 mg/kg body weight or greater. 1',2',3',4'-Tetrahydro-spiro-[oxazolidine(5,1') naphthalene]-2,4-dione is expected to show activity when administered in dosage amounts greater than 50 mg/kg body weight, where no significant activity has been observed in preliminary tests, for example when administered at doses of between about 100 and 200 mg/kg body weight.

The present invention is illustrated by the following examples. It will be understood, however, that the invention is not limited to the specific details of these examples.

EXAMPLE 1

Ethyl-1-hydroxyindan-1-carboximidate

A 100 ml ethereal solution of 1-indanone (20.0 g, 0.152 mol) (Aldrich), trimethylsilyl cyanide (21.9 g, 0.22 mol) (Silar), and zinc iodide (0.200 g, 0.001 mol) was kept at 20° C. for four days then diluted with 250 ml ether and washed with 5% sodium bicarbonate (2×100 ml). The organic phase was dried over magnesium sulfate, filtered, and evaporated in vacuo to a residue of the desired trimethylsilyl cyanohydrin and was used directly in the next step. This oily residue was dissolved in 100 ml ethanol and perfused with anhydrous hydrogen chloride while cooling at 0° C. After a 30 minute perfusion period the flask was stoppered and allowed to come to room temperature overnight. The mixture was poured into 200 ml of ice water and extracted with ethyl acetate (2×100 ml). The aqueous phase was layered with ethyl acetate, cooled to 0° and basified with 6 N sodium hydroxide. The separated basic layer was extracted with (2×100 ml) ethyl acetate. The three ethyl acetate portions were pooled, dried over magnesium sulfate, filtered, and evaporated in vacuo to an oily solid residue, 3.59 g (12%). Crystallization from hexane gave a solid which slowly melted at room temperature.

EXAMPLE 2

Spiro-[indane(1,5')oxazolidine]-2',4'-dione

The hydroxy imidate of Example 1 (2.05 g, 10.0 mmol) and N,N'-carbonyl diimidazole (1.62 g, 10.0 mmol, Aldrich) were fused at 100° C. for 16 hours. The mixture was diluted with 100 ml ethyl acetate and washed with 2×100 ml 1 N hydrochloric acid. The organic phase was extracted with 3×80 ml, 5% sodium bicarbonate. This basic phase was acidified with 6 N hydrochloric acid and extracted with 3×100 ml ethyl acetate. The solid product obtained from this organic phase after washing with 2×100 ml brine, drying over magnesium sulfate, filtration and evaporation in vacuo was recrystallized from toluene; 0.738 g (36%), mp 163°–164.5° C.

EXAMPLE 3

1-cyano-1-trimethylsilyloxy-1,2,3,4-tetrahydronaphthalene

α-Tetralone (25.0 g, 0.17 mol, Aldrich) in 100 ml ether was treated with trimethylsilyl cyanide (19.8 g, 0.20 mol, Silar) and zinc iodide (250 mg, 0.78 mmol, Ventron) at room temperature for 16 hours. After dilution to 500 ml with ether and washing with 2×100 ml 5% sodium bicarbonate and 1×100 ml brine the organic solution was dried over magnesium sulfate, filtered, and evaporated in vacuo to an oil, 40.7 g (98%).

EXAMPLE 4

1-cyano-1-hydroxy-1,2,3,4-tetrahydronaphthalene

The silyl cyanohydrin of Example 3 (40.7 g, 165 mol) was dissolved in 300 ml ethanol and perfused at 0° C. with hydrogen chloride for 30 minutes. After an additional 16 hours at 0° C. the mixture was evaporated in vacuo to an oil. This was taken up in chloroform and washed with 2×100 ml sodium bicarbonate, 1×80 ml water, 1×80 ml brine, dried over magnesium sulfate, filtered, and evaporated in vacuo to a residue which partially crystallized. This solid was triturated with 10% ethereal hexane 17.6 g (62%) mp 55°–59° C. (69°–75° C. after recrystallization from ether/hexane).

EXAMPLE 5

Ethyl-1-hydroxy-1,2,3,4-tetrahydronaphthalene-1-carboximidate

The cyanohydrin of Example 4 (6.0 g, 34.7 mmol) was dissolved in 60 ml ethanol and perfused with hydrogen chloride for 30 minutes. After a 16 hour reaction period at 0° C. the mixture was evaporated in vacuo to a solid which was triturated with ether. The residue was taken up in 200 ml chloroform and washed with 2×50 ml saturated sodium bicarbonate, 1×50 ml brine, dried over sodium sulfate, filtered, and concentrated to a solid; 5.3 g (71%), mp 84°–86° C.

EXAMPLE 6

1',2',3',4'-tetrahydro-spiro-[oxazolididine(5,1') naphthalene]-2,4-dione

The hydroxy imidate of Example 5 (2.00 g, 9.10 mmol) was dissolved in 80 ml of tetrahydrofuran and triethyl amine (1.80 g, 18.20 mmol) at 0° C. and perfused with phosgene gas for 30 minutes. The reaction mixture was warmed to 20° C. and stirred overnight. The heterogeneous mixture was poured onto 80 ml of crushed ice and the aqueous solution extracted with 2×100 ml chloroform. The combined organic phase was extracted with 2×100 ml saturated sodium bicarbonate. The basic phase was acidified to pH 1 with 6 N hydrochloric acid and extracted with 2×100 ml of ethyl acetate. The ethyl acetate was dried over sodium sulfate, filtered, and evaporated in vacuo to a solid which was recrystallized from hot toluene; 560 mg (28%), mp 170°–172° C.

EXAMPLE 7

4-Methyl-spiro-[indane(1,5')oxazolidine]-2',4'-dione

Following the procedure of Examples 1 and 2, the title compound is prepared from 4-methyl-indan-1-one (Chem. Ber. 25, 2104 (1892)).

EXAMPLE 8

6-Chloro-spiro-[indane(1,5')oxazolidine]-2',4'-dione

Following the procedure of Examples 1 and 2, the title compound is prepared from 6-chloro-indan-1-one (Bull. Soc. Chem. Fr. 1973, 3096).

EXAMPLE 9

7-Methyl-1',2',3',4'-tetrahydro-spiro-[oxazolidine(5,1') naphthalene]-2,4-dione

Following the procedures of Examples 3 to 6, the title compound is prepared from 7-methyl-α-tetralone (Monatsh Chem. 88, 517 (1957)).

EXAMPLE 10

7-Bromo-1',2',3',4'-tetrahydro-spiro-[oxazolidine(5,1') naphthalene]-2,4-dione

Following the procedures of Examples 3 to 6, the title compound is prepared from 7-bromo-α-tetralone (S.O.C. 27 76 (1962)).

I claim:

1. A compound of the formula

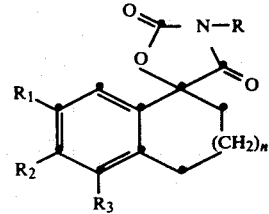

and the pharmaceutically acceptable salts thereof, wherein n is zero or one;

R and $R_2$ are each hydrogen;

and $R_1$ and $R_3$ are each selected from the group consisting of hydrogen, chloro, bromo, fluoro and alkyl of 1 to 3 carbon atoms.

2. A compound according to claim 1 wherein n is one.

3. A compound according to claim 2 wherein $R_1$ and $R_3$ are each selected from the group consisting of hydrogen, chloro, bromo, fluoro and methyl.

4. A compound according to claim 3 wherein $R_1$ and $R_3$ are each hydrogen.

5. A compound according to claim 1 wherein n is zero.

6. A compound according to claim 5 wherein $R_1$ and $R_3$ are each selected from the group consisting of hydrogen, chloro, bromo, fluoro and methyl.

7. A compound according to claim 6 wherein $R_1$ and $R_3$ are each hydrogen.

8. A pharmaceutical composition comprising a pharmaceutically acceptable carrier and a compound of claim 1 in an amount effective for the treatment of diabetes-associated complications.

9. A method for treating a diabetic host for diabetes-associated complications, which comprises administering to said host an effective amount of a compound of claim 1.